United States Patent [19]

Trick

[11] Patent Number: 4,881,530
[45] Date of Patent: Nov. 21, 1989

[54] PENILE PROSTHESIS

[75] Inventor: Robert E. Trick, Racine, Wis.

[73] Assignee: Medical Engineering Corporation, Racine, Wis.

[21] Appl. No.: 254,976

[22] Filed: Oct. 7, 1988

Related U.S. Application Data

[63] Continuation-in-part of Ser. No. 145,629, Jan. 19, 1988.

[51] Int. Cl.$^4$ ............................................... A61F 2/26
[52] U.S. Cl. ....................................................... 128/79
[58] Field of Search ............................................. 128/79

[56] References Cited

U.S. PATENT DOCUMENTS

| | | | |
|---|---|---|---|
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,201,202 | 5/1980 | Finney et al. | 128/79 |
| 4,204,530 | 5/1980 | Finney | 128/79 |
| 4,267,829 | 5/1981 | Burton et al. | 128/79 |
| 4,318,396 | 3/1982 | Finney | 128/79 |
| 4,342,308 | 8/1982 | Trick | 128/79 |
| 4,353,360 | 10/1982 | Finney et al. | 128/79 |
| 4,360,010 | 11/1982 | Finney | 128/79 |
| 4,364,379 | 12/1982 | Finney | 128/79 |
| 4,369,771 | 1/1983 | Trick | 128/79 |
| 4,383,525 | 5/1983 | Scott et al. | 128/79 |
| 4,399,811 | 8/1983 | Finney et al. | 128/79 |
| 4,399,812 | 8/1983 | Whitehead | 128/79 |
| 4,407,278 | 10/1983 | Burton et al. | 128/79 |
| 4,424,807 | 1/1984 | Evans, Sr. | 128/79 |
| 4,449,520 | 5/1984 | Palomar et al. | 128/79 |
| 4,550,719 | 11/1985 | Finney et al. | 128/79 |
| 4,550,720 | 11/1985 | Trick | 128/79 |
| 4,572,168 | 2/1986 | Fischell | 128/79 |
| 4,574,792 | 3/1986 | Trick | 128/79 |
| 4,590,927 | 5/1986 | Porter et al. | 128/79 |
| 4,594,997 | 6/1986 | Hakky | 128/79 |
| 4,596,242 | 6/1986 | Fischell | 128/79 |
| 4,622,958 | 11/1986 | Finney | 128/79 |
| 4,718,410 | 1/1988 | Hakky | 128/79 |
| 4,726,360 | 2/1988 | Trick et al. | 128/79 |

Primary Examiner—Robert Peshock
Assistant Examiner—Cary E. Stone
Attorney, Agent, or Firm—Quarles & Brady

[57] ABSTRACT

An improved penile prosthesis includes at least one elongated, flexible cylinder containing a non-distensible bladder for implantation in the pendulous penis; a pump for implantation in the scrotal sac; tubing connecting the pump to the bladder; a valve for retaining the fluid in the bladder; and, an elastic retracting cylinder positioned about the bladder. The retracting cylinder is smaller than the fully inflated bladder and stretches when the bladder is inflated. When the bladder is fully inflated and valve is opened to permit fluid to exit, the stretched retracting cylinder automatically forces fluid out of the bladder.

5 Claims, 2 Drawing Sheets

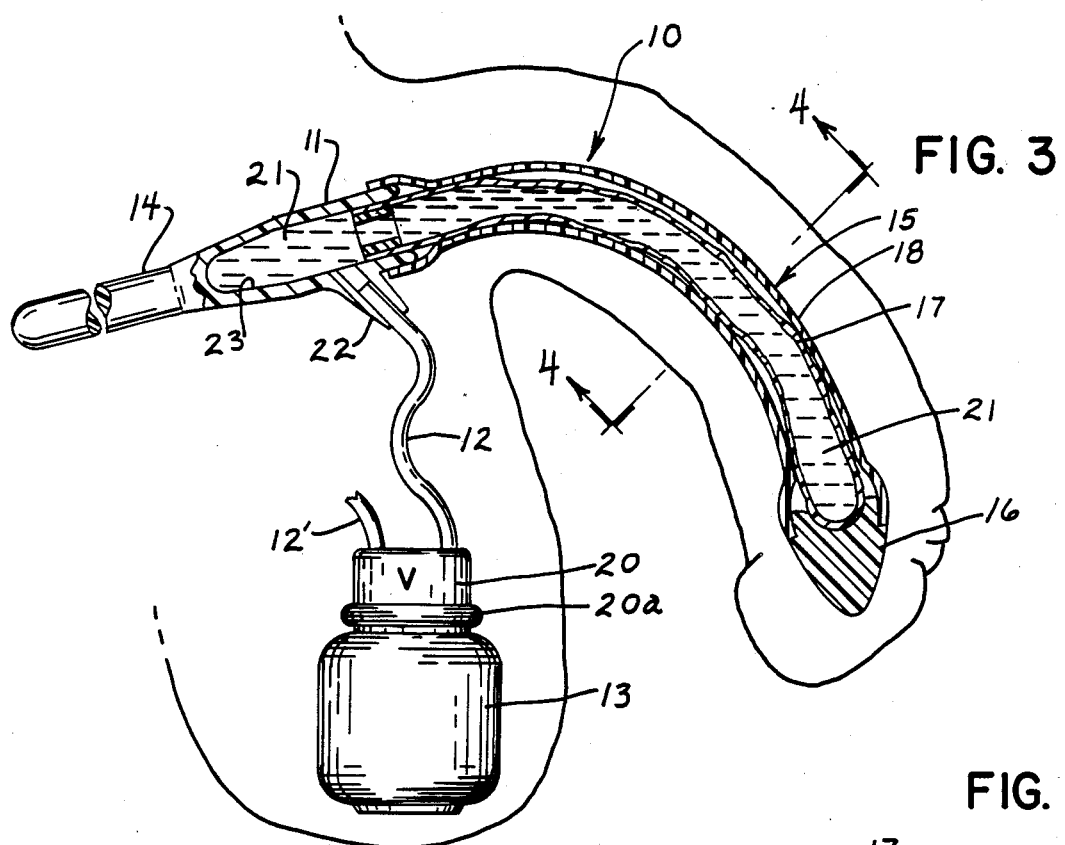
FIG. 3
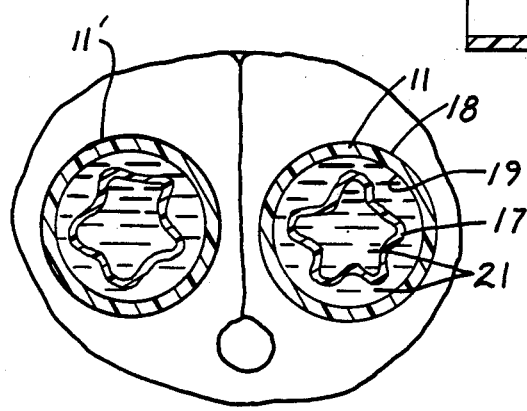
FIG. 4
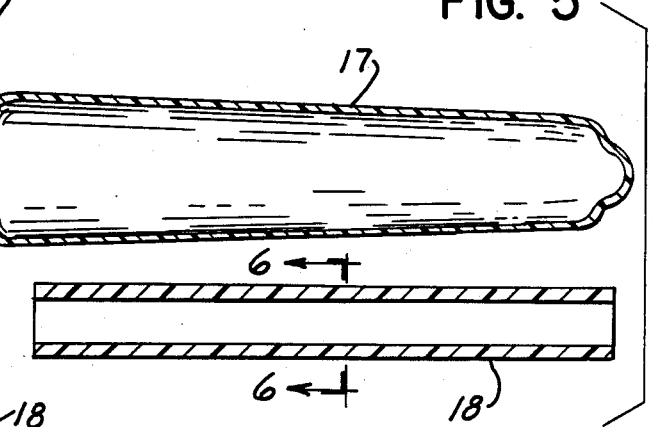
FIG. 5
FIG. 6

PENILE PROSTHESIS

RELATED APPLICATIONS

This application is a continuation in part of my co-pending U.S. patent application Ser. No. 145,629 filed Jan. 19, 1988.

FIELD OF THE INVENTION

The present invention relates to penile prostheses for curing erectile impotence. More particularly, it relates to an inflatable penile prosthesis.

BACKGROUND OF THE INVENTION

In some instances of erectile impotence in which the patient does not respond to more conventional therapy, the surgical implanting of a penile prosthesis may be the only practical means of remedying the impotency.

In the past, several types of penile prostheses have been employed. One type of prosthesis consists of a pair of rods of suitable stiffness each of which is surgically implanted into a separate corpus cavernosum of the penis. One disadvantage of the rod-type implants is that the stiffness of the rods makes it difficult to implant rods of sufficient diameter so that the penis in the erectile state will have a normal girth. The sleeve prosthesis disclosed in U.S. Pat. No. 4,204,350 is an attempt to overcome that disadvantage.

Another type of penile prosthesis which is available is the inflatable prosthesis. The most common inflatable prosthesis includes two fairly long, inflatable, distensible tubes that are surgically implanted in the corpora cavernosa of the penis. Each of the tubes is connected by tubing to a pressure bulb for inflating fluid which is implanted in the scrotal sac and a large reservoir which must be implanted in the abdominal cavity. The distensible tubes are collapsible so that they can be easily implanted and they can be inflated to increase the length and girth of the penis to approach that attained in a normal erection. The prosthesis of U.S. Pat. No. 3,954,102 is representative of this type of inflatable prosthesis.

Another type of inflatable penile prosthesis that can result in increased length and girth is the type shown in U.S. Pat. Nos. 4,009,711 and 4,201,202. It basically consists of two implants each having its own relatively large, pressurizing bulb which is surgically implanted in the scrotal sac. Each implant includes a non-distensible stem made of a relatively stiff material to support the implant and an integral, collapsible, balloon-like portion which is implanted into the corpora of the pendulous penis and inflated with a pressure bulb to affect an erection.

The recently issued Hakky U.S. Pat. No. 4,718,410 discloses a similar prosthesis which consists of two implants each with its own inflatable pressure chamber which serves as a hinge. In one embodiment, the pressure chambers are surrounded by a non-distensible bellows which permits the chamber to expand longitudinally and prevents it from expanding radially.

Recently, inflatable penile prostheses have become commercially available which like the rod-type can be implanted completely in the penis. These prostheses basically consist of a pair of cylindrical implants each containing its own pump, reservoir and pressure chamber. The pressure chambers are non-distensible so that only small amounts of fluid are needed to be transferred from the reservoirs to make them rigid. These prostheses provide many advantages, but they do not significantly increase the size of the penis. Representative of such prostheses are those shown in U.S. Pats. Nos. 4,353,360 and 4,590,927.

A need still exists for a penile prosthesis which is more natural appearing in both the flaccid and erectile states.

SUMMARY OF THE INVENTION

It is the general object of the present invention to disclose an improved inflatable penile prosthesis which appears more natural in both the flaccid and erecticle states.

It also is an object to disclose an improved inflatable penile prosthesis which automatically achieves a more natural appearing flaccid state.

The penile prosthesis of the present invention consists of at least one elongated, flexible, cylindrical implant containing a non-distensible, elongated, conical bladder, pump means and tubing connecting the bladder and pump means so that the bladder can be inflated with pressurizing fluid. The prosthesis of the present invention also includes a valve means which keeps fluid in the pressurized bladder and at least one elastic, retracting member which is positioned concentrically about the outside of the bladder.

The retracting member of the prosthesis of the present invention is smaller in diameter and shorter in length than the non-distensible bladder and it is stretched as the bladder is inflated. When the bladder is fully inflated, the retracting member is stretched to about 1.4 to about 2 times its unstretched size. When the valve means, which retains the fluid in the bladder, is opened the elastic retracting member contracts to its original size and shape and in the process forces sufficient fluid out of the bladder so that the penis automatically assumes a normal flaccid state.

In a preferred embodiment, there are two cylindrical implants each having a relatively stiff, proximal base which is implanted into the root end of a corpus cavernosum to anchor and support the implant and a flexible distal portion, which includes the non-distensible bladder and the elastic retracting member. The distal portion is implanted into the portion of the corpus cavernosum in the pendulous penis. The preferred pump means is a combined pump reservoir assembly which is implanted in the scrotal sac and connected to the bladder by the tubing.

The penile prosthesis of the present invention provides distinct advantages over previously available prostheses because it permits both the length and girth of the penis to be increased to that of a natural erection and for the penis to assume a more natural flaccid state.

BRIEF DESCRIPTION OF THE DRAWINGS

FIG. 3 is a view similar to FIG. 1, except the bladder is depressurized;

FIG. 4 is a view like FIG. 2 taken along lines 4—4 in FIG. 3;

FIG. 5 is a view showing the relative sizes of the bladder and the retracting member; and FIG. 6 is a cross-sectional view taken along lines 6—6 in FIG. 5.

DESCRIPTION OF THE PREFERRED EMBODIMENT

Figure 1:
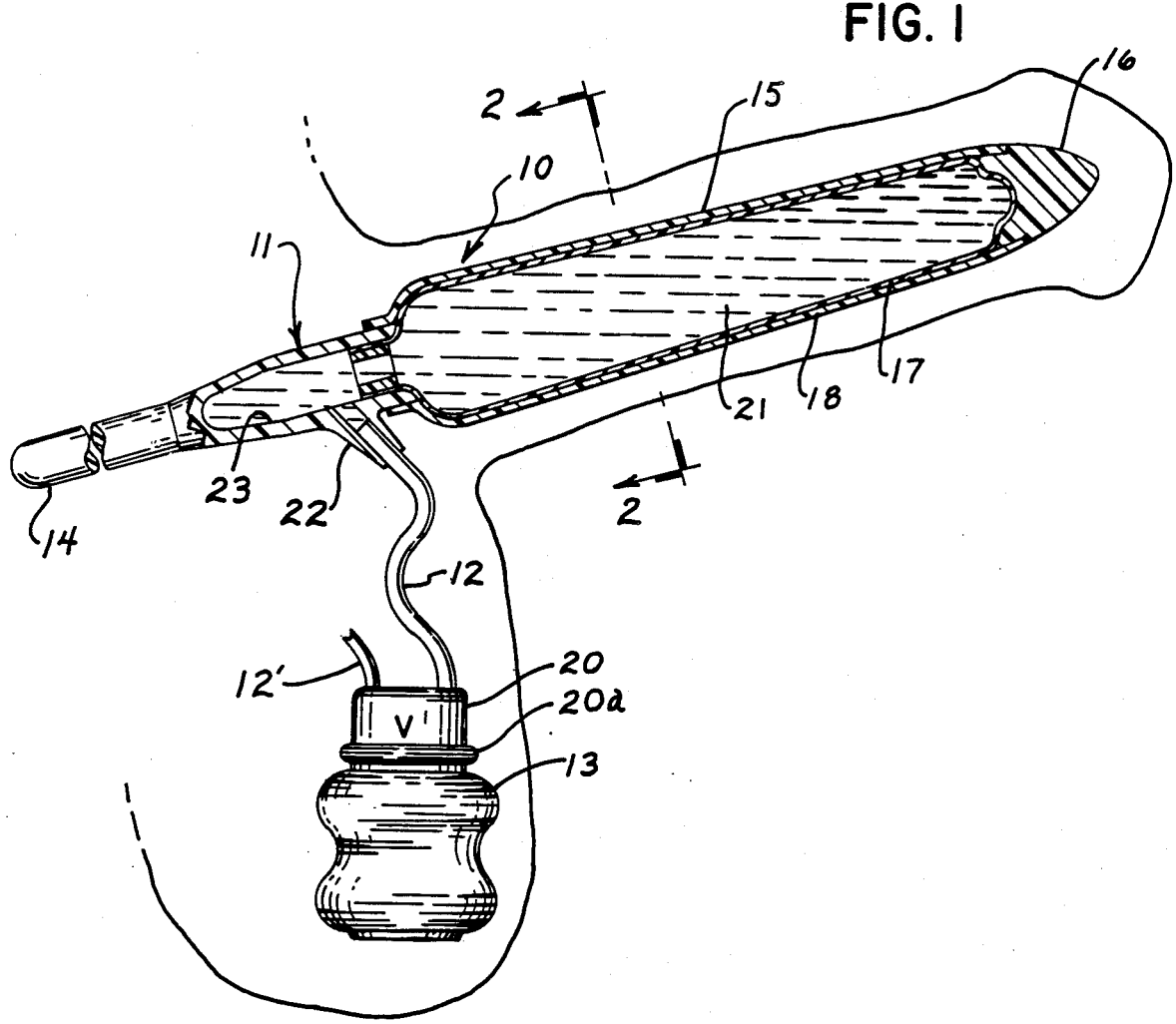
FIG. 1 is a sectional view of a penis with a penile prosthesis of the present invention with the bladder fully pressurized.

In FIGS. 1 to 4 of the drawings, a penile prosthesis 10 is shown which consists of two identical cylindrical implants 11 and 11', connecting tubing 12, 12' and a single pump reservoir assembly 13. Because the implants 11 and 11' are identical only the implant 11 will be described.

Figure 2:
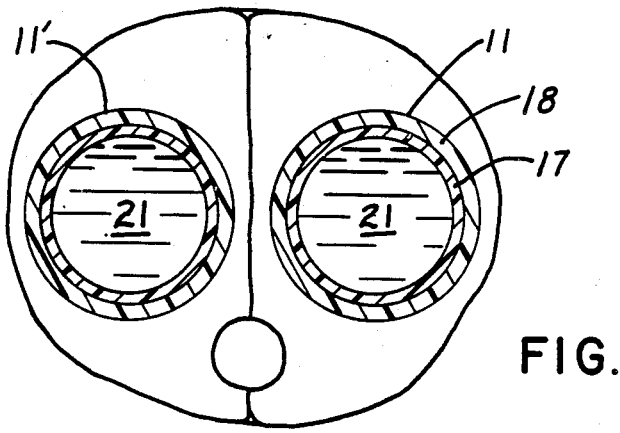
FIG. 2 is a cross sectional view taken along the lines 2—2 in FIG. 1.

The implant 11 is an elongated cylindrical member with a short, proximal base or stem 14 of relatively stiff material, which is implanted in the root end of a corpus cavernosum to support and anchor the implant, and a longer tapered distal portion 15 of a softer, more flexible material, which is implanted into the portion of the corpus cavernosum in the pendulous penis. The distal portion 15 is provided with a tip 16 which is paraboloidal in shape to conform to the inner shape of the end of the corpus cavernosum. As seen in FIGS. 2 and 4, each of the implants 11, 11' is positioned in a separate corpus cavernosum of the penis.

Still referring to FIGS. 1 to 4, it can be seen that the distal portion 15 of the implant 11 includes an elongated generally conical shaped bladder 17 and an outer retracting member 18. As seen therein, the retracting member 18 is attached at one end to the stem 14 and at the other end to the tip 16 to form a compartment 19 (seen best in FIG. 4) which contains the bladder 17 and may contain a small amount of fluid for lubrication purposes.

In FIGS. 5 and 6, the conical bladder 17 and the cylindrical retracting member 18 are shown. The bladder 17 which serves as the pressure chamber of the implant is preferably molded of a relatively inelastic material, such as a polyolefin or a polyester and it is non-distensible even when pressurized. The retracting member 18, is a cylinder of an elastic material, such as silicone rubber or a thermoplastic rubber which is smaller in diameter and shorter than the bladder 17.

The preferred retracting member 18 can have a relatively thick wall 18a, seen best in FIG. 6, so that it requires significant force to be stretched. The preferred unstretched retracting member 18 is only about ½ to about ¾ the inflated size of the bladder 17. The size and material of the retracting member 18 can vary greatly, provided the force that it exerts on the fully inflated bladder 17 is sufficient to empty enough fluid out of the bladder 17 when a valve 20 is opened to have the implant and the penis in which it is implanted assume a normal flaccid state as seen in FIG. 3 and 4. The pressure exerted on the pressurized bladder 17 by the stretched retracting member 18 will normally be equivalent to about 70 centimeters of water column to about 100 centimeters of water column.

The operation of the prosthesis 10 will now be described.

As seen in FIGS. 1 and 2, the bladder 17 in the implant 11 is in a pressurized state and full of a biocompatible hydraulic fluid 21, such as saline or a free flowing silicone gel. As seen in these views, the distal portion 15 is rigid as the result of the bladder 17 being completely filled with fluid 21 under pressure and the penis assumes an erectile position. When the bladder 17 is in this state the retracting member 18 is stretched to conform to the shape of the bladder 17.

As seen best in FIGS. 3 and 4, in the non-pressurized state, the bladder 17 is collapsed and only partially filled with fluid 21 and the retracting member 18 is not stretched. As a result, the penis is smaller in girth and length than in the pressurized erectile state seen in FIGS. 1 and 2. In addition, in the non-pressurized state the distal portion 15 of the implant 11 flexes and permits the penis to assume a substantially normal, flaccid position as seen in FIG. 3.

In the embodiment seen in FIGS. 1 and 3, the implant stem 14 is hollow and there is a port 22 which connects the hollow interior 23 of the stem 14 to the tubing 12 which leads to the pump reservoir assembly 13. The pump reservoir assembly 13 includes the valve 20 which is of the type which automatically opens when the fluid pressure in the pump reservoir assembly 13 exceeds that in the tubing 12. The valve 20 prevents the flow of fluid from the pressurized bladder 17 and tubing 12 to the pump reservoir assembly 13 until it is manually opened. The valve 20 returns the fluid in the pressurized bladder 17. The preferred valve 20 can be manually opened by squeezing the ring 20a. Suitable valves of this type are known and such valves are disclosed in U.S. Pat. Nos. 4,060,080 and 4,718,410.

When the bladder 17 is fully pressurized and the penis is in the erectile state, the penis can be returned to a normal appearing flaccid state by simply manually opening the valve 20 by squeezing the ring 20a. When this is done the elastic retracting member 18 returns to its original shape and size and forces enough of the fluid 21 in the bladder 17 back through the tubing 12, and into the pump reservoir assembly 13 to have the prosthesis assume the condition seen in FIGS. 3 and 4.

The preferred pump reservoir assembly 13 also can be provided with a septum or one-way valve (not shown), so that additional fluid can be added or removed with a hypodermic needle (not shown) even after the prosthesis has been implanted.

The preferred method of implantation of the implants is through the leading edge of the scrotum at the penile-scrotal junction. After appropriate incision, the corpus cavernosum is dilated distally and proximally to accept the implant. The approximate anatomical measurements are made to ensure that the stem of the implant will be positioned at the base of the penis below the pelvic bone. An implant having an appropriately sized distal portion is selected. The proximal stem of the implant is then cut to the appropriate length, if necessary.

The proximal stem is inserted in the root end of a dilated crus after trimming and the distal portion is inserted in the portion of the corpus cavernosum in the pendulous penis. The identical procedure is performed on the other side of the penis and the pump reservoir and tubing are implanted to complete the surgical procedure. The incisions are then closed. The stems of the two implants may diverge laterally to accommodate the anatomy and provide lateral stability to the penis.

In the preferred embodiment, all the parts and components of the prosthesis are made of medical application, biocompatible materials, which are non-reactive, non-toxic and well tolerated by the adjacent organic tissues.

It will be readily apparent to those skilled in the art, that the retracting member can provide a number of additional advantages. For example, the elastic retracting member also can serve to protect the pressure chamber from accidental puncture during surgery. In addition, although flexible it does not collapse under its own weight, therefore it provides the implant with a smooth uninterrupted outer wall even in the non-pressurized state.

The foregoing description has been for purposes of illustration only. Therefore, it will be readily apparent to those skilled in the art to which this invention relates that a variety of changes and modifications might be made without departing from the spirit and scope of the invention.

I claim:

1. A penile prosthesis comprising at least one elongated, flexible cylindrical implant to be implanted in the pendulous penis, said implant containing a non-distensible inflatable bladder; pump means to be implanted in the scrotum for inflating said bladder with fluid; tubing connecting the pump means to the bladder; valve means for retaining fluid in the bladder; and, a retracting member positioned about said bladder, said retracting member being of an elastic material and smaller than the bladder so that when the bladder is inflated with fluid the retracting member is stretched and will exert pressure upon the bladder so that when the valve is opened and the bladder is permitted to empty, the retracting member will automatically force fluid out of the bladder.

2. A penile prosthesis of claim 1 in which the bladder is generally conical shaped and it is longer than the retracting member.

3. A penile prosthesis of claim 1 in which the retracting member when stretched by the fully inflated bladder exerts a force of about 70 centimeters of water column to about 100 centimeter of water column upon the bladder.

4. A penile prosthesis of claim 1 in which the retracting member is a cylinder of elastomeric material.

5. A penile prosthesis of claim 1 in which the retracting member is flexible but does not collapse under its own weight so that it provides the implant with a smooth uninterrupted outer wall.

* * * * *